United States Patent [19]
Niki et al.

[11] Patent Number: 5,553,079
[45] Date of Patent: Sep. 3, 1996

[54] RADIO COMMUNICATION APPARATUS AND METHOD FOR MULTIPLEX TRANSMISSION OF VOICE AND DATA SIGNALS

[75] Inventors: Atsuyoshi Niki, Koganei; Tsyneyuki Minowa, Mitaka; Ichiro Maeda, Tama; Sakari Ohira, Sendai, all of Japan

[73] Assignees: Hitachi Denshi Kabushiki Kaisha, Tokyo; Tohoku Electric Power Co., Inc., Miyagi-ken, both of Japan

[21] Appl. No.: 413,265

[22] Filed: Mar. 30, 1995

[30] Foreign Application Priority Data

Apr. 4, 1994 [JP] Japan .................................. 6-089156

[51] Int. Cl.⁶ ........................................................ H04J 3/18
[52] U.S. Cl. ............................................ 370/110.4; 370/118
[58] Field of Search ................................ 370/110.4, 111, 370/112, 118, 109, 71; 381/31, 34, 35; 375/216

[56] References Cited

U.S. PATENT DOCUMENTS

4,328,579  5/1982  Hashimoto et al. .................. 370/110.4
4,864,566  9/1989  Chauveau .............................. 370/111
5,136,586  8/1992  Greenblatt ........................ 370/110.4

Primary Examiner—Douglas W. Olms
Assistant Examiner—Ajit Patel
Attorney, Agent, or Firm—Antonelli, Terry, Stout & Kraus

[57] ABSTRACT

A radio communication apparatus for transmitting a voice signal and a data signal in a multiplex form. The transmitting side of the radio communication apparatus includes: a sampling unit for sampling the voice signal and the data signal and generating a digital voice signal and a digital data signal; a time division unit for dividing the digital voice signal and the digital data signal on the basis of a predetermined period; a modulation unit for modulating the divided digital data signal by a predetermined digital modulation scheme; a unit for compressing the divided digital voice signal at a predetermined compression factor and generating a compressed voice signal; a unit for combining the divided and compressed voice signal and the divided and digitally modulated digital data signal and generating a multiplex signal; and a unit for modulating a carrier signal by the multiplex signal and transmitting the modulated carrier signal as a transmission signal.

22 Claims, 6 Drawing Sheets

RADIO COMMUNICATION APPARATUS AND METHOD FOR MULTIPLEX TRANSMISSION OF VOICE AND DATA SIGNALS

BACKGROUND OF THE INVENTION

The present invention relates to multiplex transmission of voice (talk signals) and data signals, and more particularly to a radio communication apparatus and method suitable for transmission of vital sign signals of a patient such as electrocardiograms, pulse waves, and blood pressures from a mobile station such as an ambulance car to a base station such as an emergency control center and an emergency hospital, while having voice communications therebetween.

Multiplex transmissions by frequency division multiplex and time division multiplex have been used as a technique of multiplex transmission of both data signals such as vital sign signals and voice signals between a mobile station such as an ambulance car and a base station.

Figure 5:
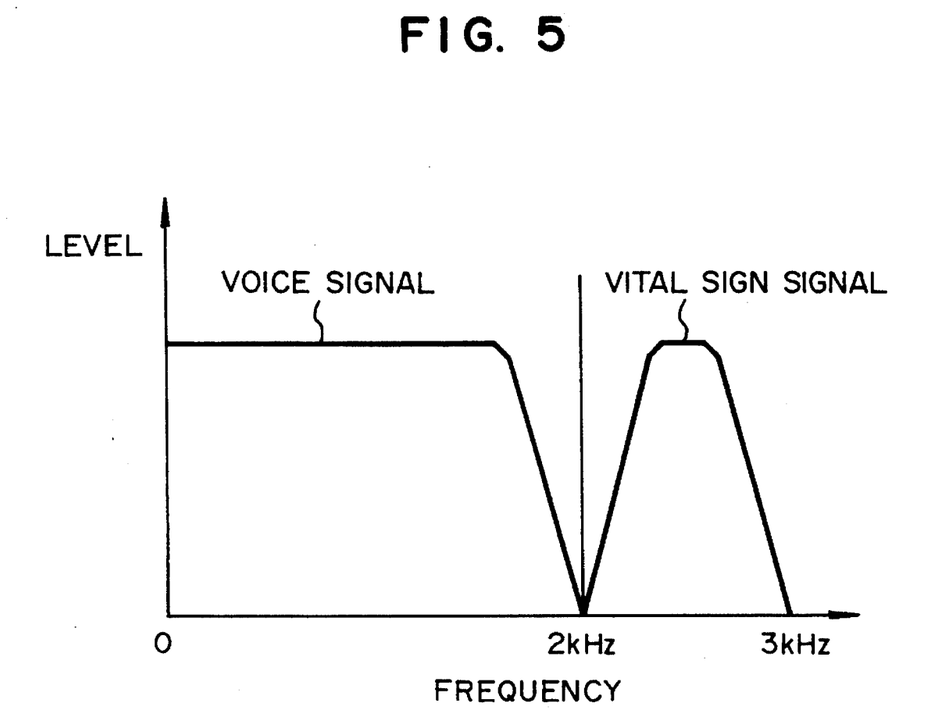
FIG. 5 is a graph showing an example of spectrum distribution of a multiplex signal used by conventional multiplex transmission by frequency division multiplex.

As illustratively shown in FIG. 5, with the multiplex transmission by frequency division multiplex, a voice signal is allocated with a band width of 300 Hz to 2 kHz and a data signal such as a vital sign signal is allocated with a band width of 2 to 3 kHz. Under this band width limit, a composite signal of the voice and data signals is transmitted over a carrier wave of a single frequency. However, since the allocated band width is narrow, the voice and data signals cannot be separated completely at a destination station and high frequency components of the voice signal are superposed on the data signal. Therefore, frequency division multiplex is almost impractical for such application.

As multiplex transmissions by time division multiplex, the following techniques, for example, are known.

(1) Japanese Patent Laid-open Publication JP-A-5-37420 entitled "Medical Information Radio Transmission Method"

(2) IEEE TRANSACTIONS ON VEHICLE TECHNOLOGY, VOL. VT-33, NO. 3, pp. 205–213 entitled "C900—An Advanced Mobile Radio Telephone System with Optimum Frequency Utilization"

A multiplexing/demultiplexing method of the medical information radio transmission method described in the document (1) will be explained with reference to FIGS. 6 and 7.

Figure 6:
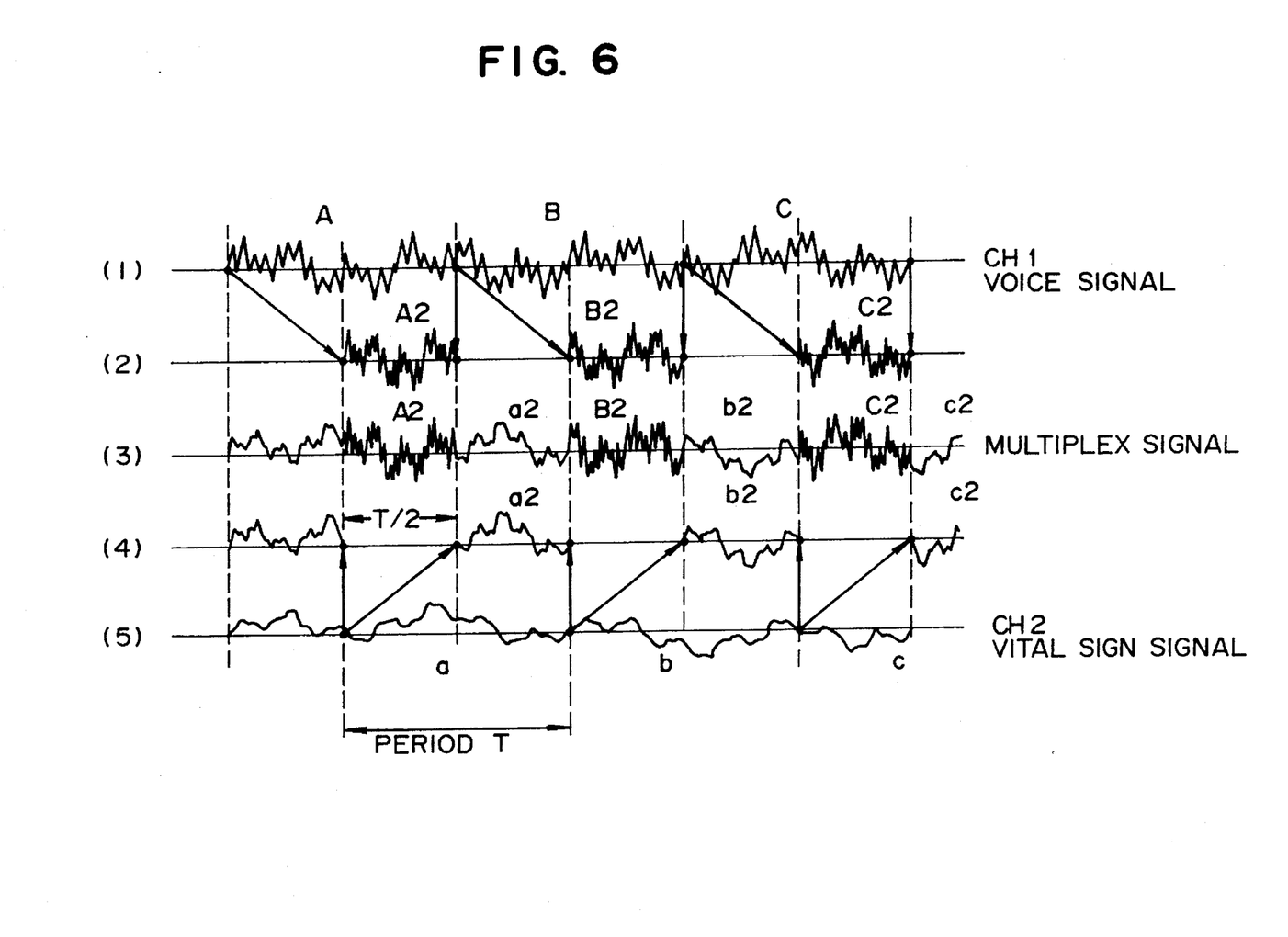
FIG. 6 is a timing chart of signals explaining a conventional multiplexing method for multiplex transmission by time division multiplex.
Figure 7:
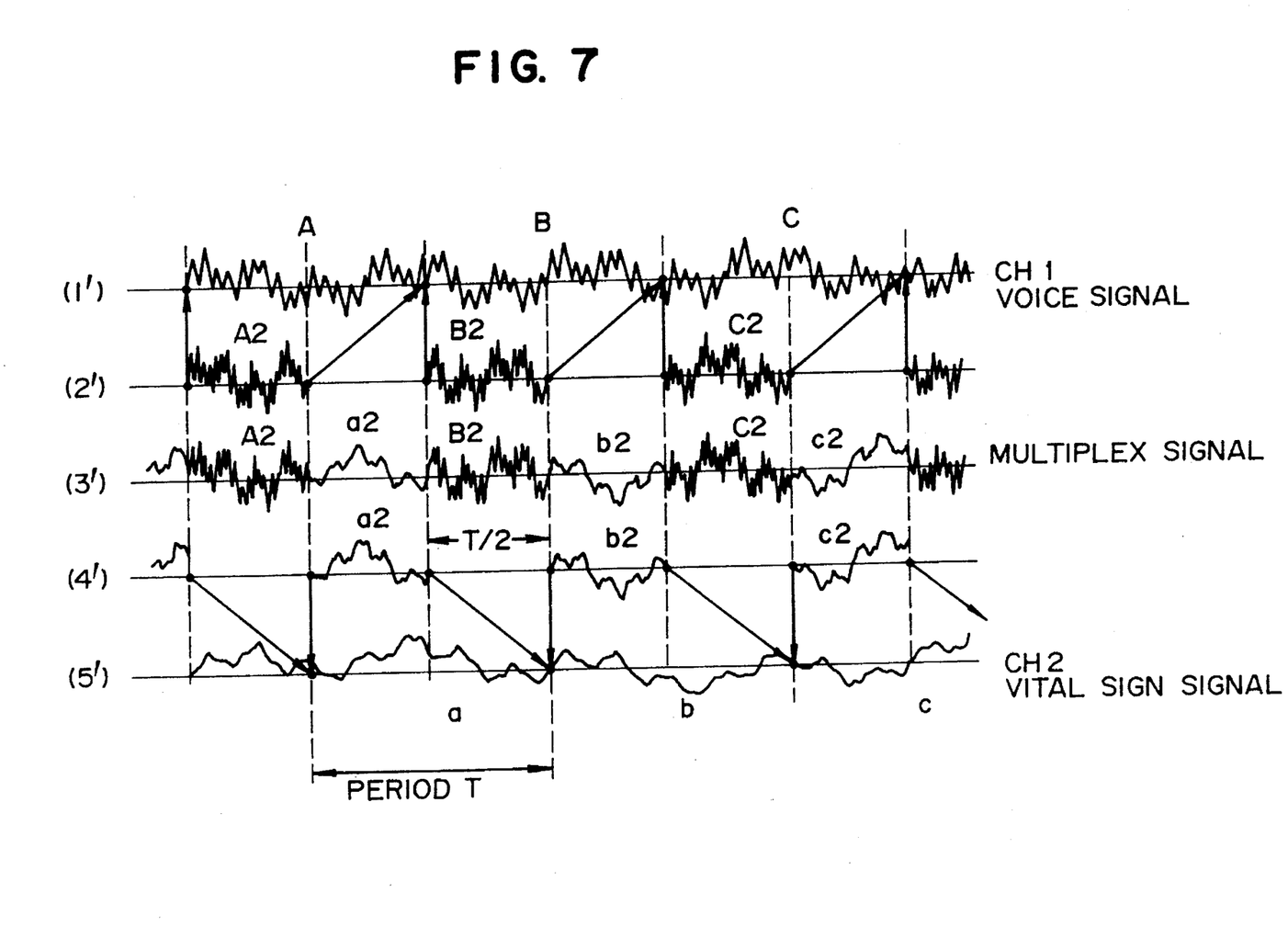
FIG. 7 is a timing chart of signals explaining a conventional demultiplexing method for radio transmission by time division multiplex.

As shown in FIG. 6, vital sign signals and voice signals are multiplexed on a transmission side (mobile station) in the following manner. A plurality of channel signals including a vital sign signal (5) and a voice signal (1) and FM modulated on a subcarrier are divided into time slots. The time slots of the vital sign and voice signals are compressed in time by a half to obtain compressed signals (2) and (4). The compressed signals are combined to form a composite multiplex signal (3). The composite multiplex signal modulates a carrier signal which is transmitted as radio waves. As shown in FIG. 7, the multiplex signal is demultiplexed on a reception side (base station) in the following manner. The received radio wave is demodulated into a composite multiplex signal (3') which is then separated into a modulated voice signal (2') and a modulated vital sign signal (4') of each channel. The modulated voice and vital sign signals are expanded in time by a twofold to obtain the original channel signals (1') and (5'). The subcarrier is demodulated to obtain the original vital sign and voice signals. A voice signal is transmitted from the base station to the mobile station by using a radio frequency different from that used for transmission of the multiplex signal from the mobile station to the base station.

In the case of the radio transmission method described in the document (2), a voice signal is divided into predetermined time slots on the transmission side (mobile station), and each time slot is compressed in time to about 90%. A data signal is directly inserted in vacant time slots formed by the time compression, in units of one block of, for example, four bits of data bursts. A carrier signal is modulated by a composite multiplex signal of the data signal and voice signal, and the modulated signal is transmitted as radio waves. On the reception side (base station), the received radio waves are demodulated to obtain a composite multiplex signal which is then separated into the original data signal and the compressed voice signal. The compressed voice signal is expanded in time to obtain the original voice signal.

The following problems are, however, associated with the conventional multiplex transmission by time division multiplex.

(a) The pass band of a transmission signal over a radio channel is generally in the range of about 300 Hz to 3 kHz. A data signal to be transmitted, such as an electrocardiogram signal, has in some cases very important information outside of the pass band, such as lower than 100 Hz. Therefore, if electrocardiogram data itself is transmitted without any processing, the very important information cannot be transmitted and is unable to be used in practice. No countermeasure for solving this problem is disclosed in the radio transmission method of the document (2).

With the medical information transmission method of the document (1), a subcarrier of about 1.1 kHz is modulated by a vital sign signal through analog FM modulation and then time compression is performed on the mobile station side. On the base station side, the subcarrier is demodulated to obtain the original vital sign signal. Since the subcarrier is modulated through analog FM modulation, the mobile station is required to have an analog FM modulator, a subcarrier signal generator, an analog synthesizer for synthesizing the compressed voice signal and data signal, whereas the base station is required to have an analog FM demodulator and a subcarrier signal demodulating circuit. However, an analog signal processing circuit is generally expensive and difficult to make it compact. Therefore, the transmission/reception apparatus becomes very bulky, heavy in weight, and high in cost. It is also difficult to transport the apparatus and install it at the mobile station, particularly at an ambulance car which has a limited mount space.

(b) In multiplex transmission of a voice signal and a data signal, it is necessary to set a compression factor of the voice signal as high as possible in order to allow the data signal to occupy a large space in the multiplex signal and in order to raise a data transmission rate. On the contrary, in order to have a good sound quality of a reproduced voice signal, it is necessary to set the compression factor as low as possible. An optimum compression factor solving the problem of this trade-off must be set in order to perform good multiplex transmission. However, the above conventional techniques use fixed compression factors of a voice signal and a data signal, irrespective of the characteristics of a transmission signal. Therefore, either the sound quality of a reproduced signal or a data transmission rate is sacrificed or becomes insufficient for practical use at worst.

SUMMARY OF THE INVENTION

The present inventor has studied multiplex transmission of a voice signal and a data signal and has found that good multiplex transmission can be achieved in the following manner, while using a very small transmission/reception apparatus. On the receiving side, in multiplexing a voice signal and a data signal having important information outside of the pass band of a communication channel such as an electro-cardiogram signal, the voice signal and data signal are sampled and the sampled signal is divided in time on the basis of a predetermined period. The data signal is then compressed, for example, by delta modulation, and the compressed data is subjected to a predetermined digital modulation process such as Minimum Shift Keying (MSK) modulation. The voice signal is compressed in time at a predetermined compression factor. The compressed voice signal and digitally modulated data signal are combined in the form of digital signal. In the demultiplexing process on the receiving side, the operations as above are performed in the reverse order.

The inventor has also found that optimum multiplex transmission is possible which satisfies both the sound quality of a reproduced voice signal and the data transmission rate, if the compression factors of the voice and data signals are determined in accordance with the frequency of the data signal to be transmitted.

A first object of the present invention is to provide a multiplex communication apparatus for voice and data signals capable of reliably transmitting a multiplex signal even if the data signal contains important information outside of the pass band of a communication channel and capable of being manufactured to be very compact, light in weight, and cost effective.

A second object of the present invention is to provide a multiplex communication apparatus for voice and data signals capable of setting an optimum compression factor from the viewpoint of both the sound quality of a reproduced voice signal and the data transmission rate.

A third object of the present invention is to provide a radio communication method for multiplex transmission of voice and data signals, particularly suitable for transmission of data signals such as electrocardiograms, pulse waves, brain waves, and blood pressures, over a radio channel.

A fourth object of the present present invention is to provide a radio communication method capable of reproducing voice and vital sign signals without any interception even if the reception side cannot detect a synchronizing signal used for separating a multiplex signal into voice and vital sign signals.

A fifth object of the present invention is to provide a communication system for multiplexing voice and vital sign signals and transmitting a multiplex signal between a base station and a mobile station via a radio channel, while allowing a transmitter at the base and mobile stations to be manufactured to be very compact, light in weight, and cost effective.

According to a first aspect of the present invention, there is provided a multiplex communication apparatus having a transmitter and a receiver. The transmitter includes: a unit for sampling a plurality of channel signals including a voice signal and a data signal; a unit for dividing in time the sampled signal on the basis of a predetermined period; a unit for subjecting the data signal to a data compression process and generating a compressed data signal; a unit for modulating the compressed data signal through predetermined digital modulation; a unit for compressing the voice signal at a predetermined compression factor and generating a compressed voice signal; a unit for combining the compressed voice signal and the compressed and digitally modulated data signal and generating a multiplex signal; and a unit for modulating a carrier signal by the multiplex signal and transmitting the modulated carrier signal. The receiver includes: a unit for receiving the modulated carrier signal and demodulating the multiplex signal; a unit for sampling and demultiplexing the multiplex signal; a unit for demodulating the data signal by predetermined digital demodulation, a unit for subjecting the demodulated data signal to an expanding process for the data compression process and reproducing the data signal; and a unit for expanding the voice signal at an expansion factor which is an inverse of the compression factor. According to the first aspect of the invention, the first object of the invention can be achieved.

According to a second aspect of the present invention, in the multiplex communication apparatus, the compression factor of the voice signal is set to $1-(n \times f/f_2)$ where n is a positive integer, f is the frequency of the data signal, and f2 is the modulation rate necessary for the digital modulation scheme. According to the second aspect, the second object of the present invention can be achieved.

According to a third aspect of the present invention, there is provided a communication method for a radio communication system having a base station and a mobile station connected to the base station over a radio channel. A communication method for the base station includes the steps of: sampling a plurality of channel signals including a voice signal and a vital sign signal and dividing in time the sampled signal on the basis of a predetermined period; modulating the vital sign signal by a delta modulation scheme or an adaptive delta modulation scheme to compress data; modulating the compressed vital sign signal by an MSK modulation scheme; compressing the voice signal at a predetermined compression factor and generating a compressed voice signal; combining the compressed voice signal and the MSK modulated vital sign signal and generating a multiplex signal; and modulating a carrier signal by the multiplex signal and transmitting the modulated carrier signal as a first radio wave. A communication method for the base station includes the steps of: receiving the first radio wave and demodulating the multiplex signal; sampling the demodulated multiplex signal and demultiplexing the sampled signal; subjecting the vital sign signal to a demodulating process for the MSK modulating scheme to reproduce the vital sign signal; and expanding the voice signal at an expansion factor which is an inverse of the compression factor. The base station modulates a carrier signal by the voice signal and transmits the modulated carrier signal as a second radio wave, whereas the mobile station receives and demodulates the second radio wave to reproduce the voice signal from the base station. According to the third aspect, the third object of the present invention can be achieved.

According to a fourth aspect of the present invention, in the communication method, the mobile station adds a synchronizing signal to the multiplex signal at the predetermined period, and transmits the carrier signal modulated by the multiplex signal with the synchronization signal as the first radio wave to the base station, whereas the base station receives the first radio wave, detects the synchronizing signal, demultiplexing the multiplex signal in accordance with the detected synchronizing signal, and if the synchronizing signal cannot be detected in a predetermined time, calculates the boarder between the voice signal and vital sign signal in accordance with a signal from a timer synchronizing with the period of the synchronizing signal, and demultiplexing the multiplex signal in accordance with the calculated boarder. According to the fourth aspect, the fourth object of the present invention can be achieved.

According to a fifth aspect of the present invention, there is provided a communication system having a base station and a mobile station connected to the base station over a radio channel. The base station includes a transmitter and a receiver, the transmitter including a first unit for sampling a plurality of channel signals including a voice signal and a vital sign signal; a second unit for dividing in time the sampled signal on the basis of a predetermined period; a third unit for modulating the sampled signal of the vital sign signal by a delta modulation scheme or an adaptive delta modulation scheme to compress data; a fourth unit for modulating the compressed vital sign signal by an MSK modulation scheme; a fifth unit for compressing the voice signal at a predetermined compression factor and generating a compressed voice signal; a sixth unit for combining the compressed voice signal and the MSK modulated vital sign signal and generating a multiplex signal; and a seventh unit for modulating a carrier signal by the multiplex signal, transmitting the modulated carrier signal as a first radio wave, the transmitter including an eighth unit for receiving a second radio wave transmitted and reproducing a voice signal. The base station includes a receiver and a transmitter, the receiver including: a ninth unit for receiving the first radio wave and demodulating the multiplex signal; a tenth unit for sampling the demodulated multiplex signal; an eleventh unit for demultiplexing the sampled multiplex signal and separating the sampled multiplex signal into the voice signal and the vital signa signal; a twelfth unit for subjecting the vital sign signal to a demodulation process for the MSK modulation scheme; a thirteenth unit for subjecting the demodulated vital sign signal to a demodulation process for the delta modulation scheme or the adaptive delta modulation scheme to reproduce the vital sign signal; and a fourteenth unit for expanding the voice signal at an expansion factor which is an inverse of the compression factor to reproduce the voice signal, the transmitter including a fifteenth unit for modulating a carrier signal by the voice signal and generating and transmitting the second radio wave. According to the fifth aspect, the fifth object of the present invention can be achieved.

In the operation of the multiplex communication apparatus of this present invention, the apparatus achieves very fine multiplex transmission for voice and data signals, even if a data signal to be transmitted, such as an electrocardiogram signal, has important information outside of the pass band of a communication channel. Specifically, on the transmission side, the data signal is compressed through modulation such as delta modulation. The compressed data signal is subjected to a predetermined digital modulation process such as MSK modulation to transform it into a signal suitable for the characteristics of a communication channel. This signal is then combined with a compressed voice signal to generate a multiplex signal. On the reception side, the multiplex signal is demultiplexed and demodulated by performing the above operations in the reverse order.

In the multiplexing process on the transmission side, both the voice signal and vital sign signal are sampled, and the sample signal is subjected to the time division process, data compression process, digital modulation process, time compression process for the voice signal, and synthesizing process for the voice and vital sign signals. These processes are all performed by using digital signals. The digital signal processing can be realized by using simple means such as a microprocessor and a RAM. Therefore, it is possible to provide a very compact transmitter. Similarly, in the demultiplexing process on the receiving side, the process of demultiplexing the multiplex signal and separating it into the voice signal and data signal, the process of demodulating the data signal by the digital modulation scheme, the process of subjecting the modulated data signal to a recovery process for the data compression process, and the process of expanding the voice signal at an expansion factor which is an inverse of the compression factor and reproducing the voice signal, are all performed by using digital signals. The digital signal processing can be realized by using simple means such as a microprocessor and a RAM. Therefore, it is possible to provide a very compact receiver.

DESCRIPTION OF THE PREFERRED EMBODIMENTS

Embodiments of the present invention will be detailed with reference to FIGS. 1 to 4. In the embodiments, radio communication applied to a particular case will be described wherein vital sign signals of a patient such as electrocardiograms, pulse waves, and blood pressures are transmitted from a mobile station such as an ambulance car to a base station such as an emergency hospital, while having voice communications therebetween.

Figure 1:
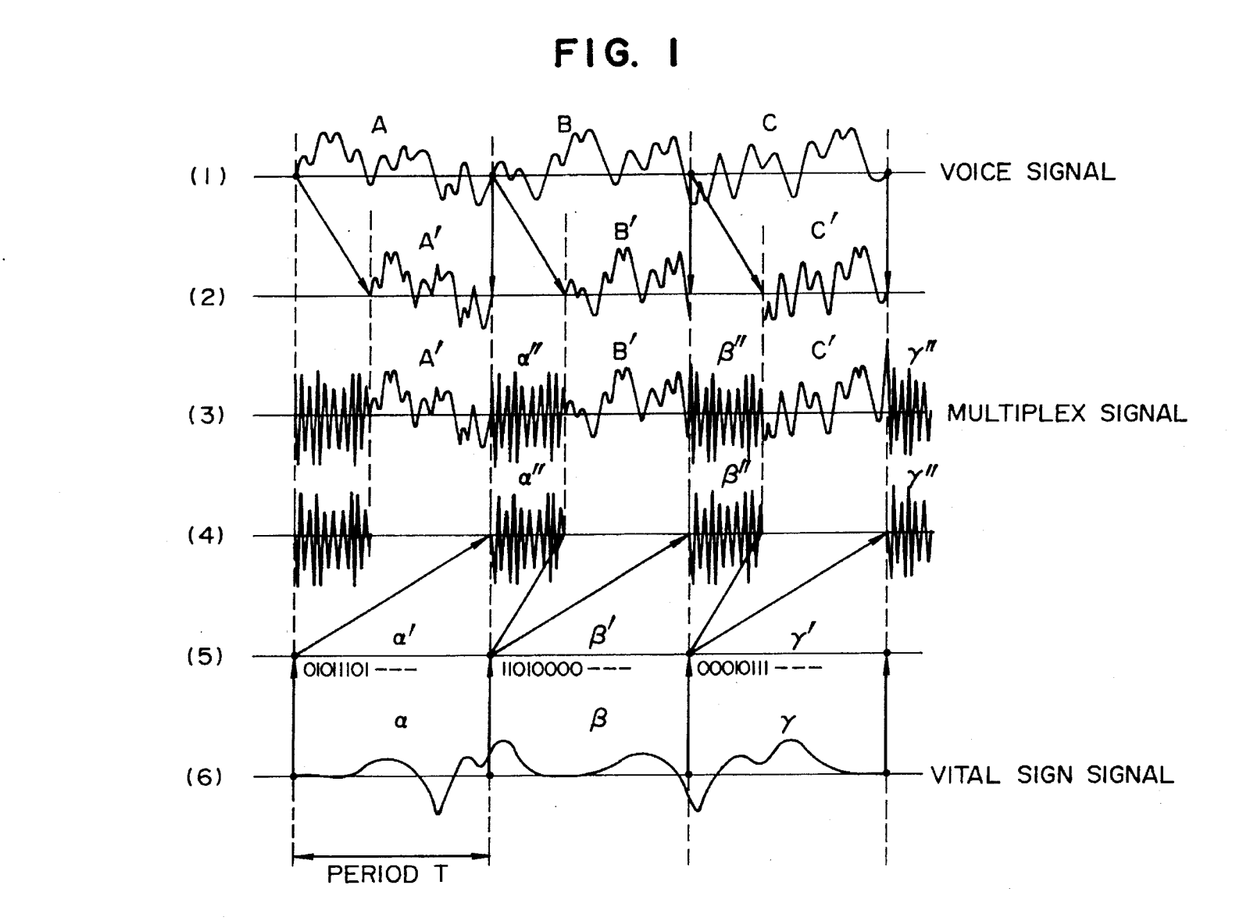
FIG. 1 is a timing chart of signals explaining a multiplexing method according to an embodiment of the invention.

A method for multiplexing a vital sign signal with a voice signal on the mobile station side (transmitting side) such as an ambulance car will be described with reference to signals (1) to (6) shown in FIG. 1. The abscissa of FIG. 1 represents time. In this example, as a fundamental case embodying the present invention, one channel of a voice signal and one channel of a vital sign signal are used. A signal (1) is a voice signal, and a signal (6) is a vital sign signal. Although a voice signal (2), a vital sign signal (4) are depicted as an analog signal in order to make the description be understood easily, they are actually a digital signal.

The analog vital sign signal (6) is sampled to transform it into a digital signal. This digital vital sign signal is divided in time by a predetermined period T into frames $\alpha$, $\beta$, $\gamma$, . . . These frames are compressed, for example, through delta modulation to obtain data trains (5) of $\alpha'$, $\beta'$, $\gamma'$, . . . These data trains are modulated through MSK modulation to obtain signals (4) of $\alpha''$, $\beta''$, $\gamma''$, . . . Assuming that the sampling rate of delta modulation is $f_1$ and the modulation rate of MSK modulation is $f_2$, the time duration of each of $\alpha''$, $\beta''$, $\gamma''$, . . . becomes $t \times (f_1/f_2)$ because delta modulation and MSK modulation is performed at one bit per one sampling. For example, if $f_1$ is 200 Hz and $f_2$ is 1200 bps, then the signal transmission time can be shortened by $T \times (200/1200) = T/6$.

Delta modulation is one of data compression methods. Other modulations such as Adaptive Delta Modulation (ADM) and Continuously Variable Delta Modulation (CVSD) may also be used so long as they can compress data so that a data signal can be inserted into a space time slot generated by the time compression process of a voice signal. MSK modulation is one of digital modulation methods for modulating a vital sign signal and changing it to a signal suitable for the characteristics of a transmission channel. Other digital modulation methods such as Frequency Shift Keying (FSK) and Phase Shift Keying (PSK) can be also used. In such digital modulation method, a carrier signal is modulated by a digital transmission data.

Each of these modulation methods is widely known in this field of technology, and is not explained in this specification. For example, the following documents may be referred to for the details of each modulation method.

(1) Delta modulation and adaptive delta modulation: "Computer Voice Processing", Electronic Science Series, issued by Sanpou Shuppan Kabushiki Kaisha, on Jun. 10, 1980, pp. 23–36.

(2) MSK, FSK, PSK: "Digital Modulation and Demodulation Technique for Mobile Communication", issued by Kabushiki Kaisha Torikeps, on Mar. 14, 1990, pp. 79–86, pp. 44–48, and pp. 48 to 50.

Next, similar to the vital sign signal, the analog voice signal (1) is sampled to transform it into a digital sound signal. This digital sound signal is divided in time by the period T into frames A, B, C, . . . These frames are compressed in time to obtain signals (2) of A', B', C', . . . In this example, the compression factor is $1-(f_1/f_2)$. For example, assuming that $f_1$ is 200 Hz and $f_2$ is 1200 bps, the compression factor is 5/6.

The intermittent signals (2) and (4) are combined to form a series of consecutive multiplex signals A', α", B', β", C', γ", . . .

Figure 2:
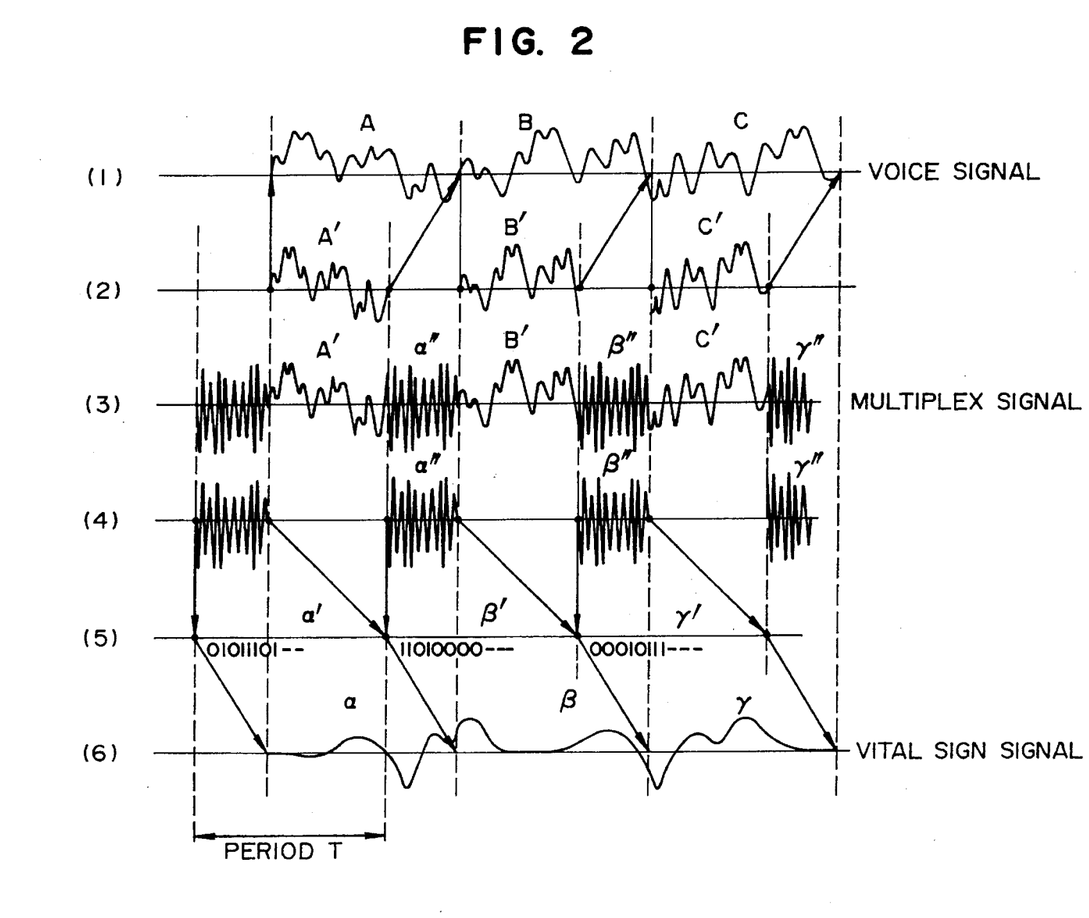
FIG. 2 is a timing chart of signals explaining a demultiplexing method according to an embodiment of the invention.

Next, a demultiplexing method for a multiplex signal according to an embodiment of the present invention will be described with reference to FIG. 2. A series of multiplex signals A', α", B', β", C', γ", . . . received at the base station side (receiving side) can be demultiplexed to reproduce the original voice signal and vital sign signal, by performing the above-described operations in the reversed order as illustrated in FIG. 2. Referring to FIG. 2, the received and demodulated multiplex signal (3) is divided by the period T. The divided multiplex signal is separated into intermittent compressed voice signals (2) and intermittent MSK modulated vital sign signals (4), in accordance with respective time durations. The vital sign signal is MSK demodulated to obtain a data train (5) which is then demodulated through delta modulation. The obtained signals are combined to reproduce the original vital sign signal (6). The compressed voice signals (2) are expanded by an inverse of the compression factor used by the time compression process and combined to reproduce the original voice signal (1).

In transmitting the multiplex signal (3) shown in FIGS. 1 and 2 over a radio channel, a transmitter having the pass band of 0.3 to 3 kHz is generally used. Therefore, the band width of a reproduced voice signal after expansion is 0.3× (compression factor) to 3×(compression factor) kHz. By using the sampling rate $f_1$ and the MSK modulation rate $f_2$, the band width of the reproduced voice signal becomes $0.3 \times (1-f_1/f_2)$ to $3 \times (1-f_1/f_2)$ kHz. Namely, with a lower $f_1$ and a higher $f_2$, the band width of a reproduced voice signal becomes broader and a good sound quality can be obtained. Therefore, a minimum sampling rate necessary for transmission and reproduction of main frequency components of a vital sign signal can be set and a maximum MSK modulation rate capable of transmitting a signal over a radio channel from a transmitter can be set. The compression factor is determined from the minimum sampling rate and the maximum MSK modulation rate. In this manner, optimum multiplex communication becomes possible which satisfies both the sound quality of a voice signal and a necessary data transmission rate.

In order to reproduce a vital sign signal having a frequency of f, it is necessary to set the sampling rate $f_1$ higher than the vital sign signal, for example, by about 10 times. Assuming that the vital sign signal can be reproduced if it is sampled at the sampling rate of 10f, the sampling rate $f_1$ of 10f is used. The MSK modulation rate is generally 1200 bps or 2400 bps. Assuming that the MSK modulation rate is 1200 bps, the compression factor is 1–10f/1200.

Consider now an electrocardiogram picked up by a defibrillator or the like used as vital sign information. An original of such an electrocardiogram signal can be reproduced up to a highest frequency in 20 Hz. Assuming that f=20 Hz and the MSK modulation rate is 1200 bps, the compression factor of a voice signal is 1–10×20/1200=83% which shows a sufficient reproducibility of a voice signal. An optimum compression factor of a voice signal is given by $1-(n \times f/f_2)$ where n is $f/f_1$, f is the frequency of the original vital sign signal, and $f_1$ is the sampling frequency.

Referring to FIG. 2, in order to divide the multiplex signal (3), it is necessary to detect the start of each frame (multiplex signal during one period T). A synchronizing signal is added to the head of, for example, each MSK modulated vital sign signal α", β", γ", . . . when the multiplex signal (3) shown in FIG. 1 is generated at a mobile station. This synchronizing signal can be generated by a method used in general, and may be a tone signal, an MSK modulated data train, or other signals. At the base station, the multiplex signal is divided by detecting the synchronizing signal. If the synchronizing signal cannot be detected at the base station, both the vital sign signal and voice signal cannot be reproduced, and the signals are lost. This problem can be solved by the following method. The base station is provided with a timer for generating a reference signal at an interval of the period of the synchronizing signals. The period of the reference signal is calibrated when the synchronizing signal is received. If there is a frame whose synchronizing signal cannot be detected, the head of the frame is designated by using the reference signal of the timer to divide the multiplex signal. In this manner, even if there is a frame whose synchronizing signal cannot be detected, the vital sign signal and voice signal can be reproduced.

Figure 3:
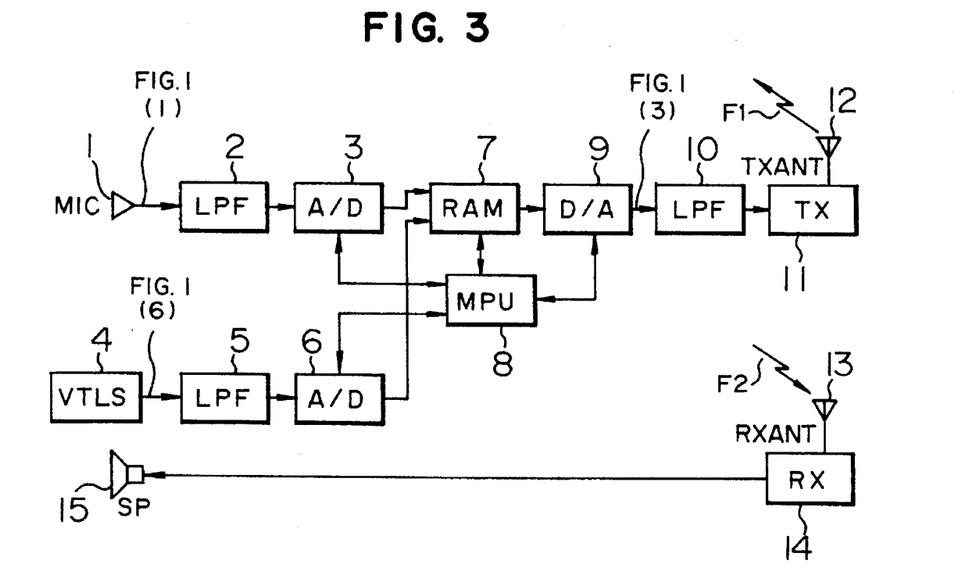
FIG. 3 is a block diagram showing the structure of a mobile station (multiplex signal transmitting side) according to an embodiment of the invention.

FIG. 3 shows the structure of a mobile station according to an embodiment of the invention. The operation to be performed by the mobile station will be described. A voice signal from a microphone (MIC) 1 at the mobile station (multiplex signal transmitting side) is passed through a low pass filter (LPF) 2, converted into a digital signal by an analog/digital converter (A/D) 3 under the control of a microprocessor (MPU) 8, and stored in a random access memory (RAM) 7. Similarly, a vital sign signal (VTLS) 4 is passed through an LPF 5, converted into a digital signal by an A/D converter 6 under the control of MPU 8, and stored in RAM 7. Of these digital signals, the vital sign signal is subjected to a data compression process such as delta modulation, ADM modulation, and CVSD modulation by controlling data access to a memory region of RAM 7 in accordance with a signal processing program. Synchronizing signal data is added to the vital sign signal subjected to the data compression process. This is performed by MPU 8 which accesses the memory region of RAM 7 in accordance with the signal processing program.

The digital compressed vital sign signal with the synchronizing signal added thereto is transformed into a digital vital sign data train for a predetermined digital modulation such as MSK, by MPU 8 in accordance with the signal processing program in the memory region of RAM 7.

More precisely the digital vital sign data train is transformed by a D/A converter 9 into an analog signal which is modulated by the predetermined digital modulation such as MSK. Before the D/A conversion, the digital vital sign data train is added to the digital voice signal in the memory of RAM 7, and MPU 8 performs a process for smoothing the boarders between the vital sign signals and voice signals. The data subjected to the above processes is temporarily stored in RAM 7. The data stored in the memory region of RAM 7 is then read at the sampling rate by which one frame is read, and converted into an analog signal by the D/A converter 9 under the control of MPU 8 to obtain a series of multiplex signals. The multiplex signal is passed through a LPF 10, and supplied to a transmitter (TX) 11 whereat a carrier signal having a frequency $F_1$ (e.g., near 371 MHz) is modulated by the multiplex signal and transmitted via an antenna (TXAN) 12 as radio waves. A voice signal from the base station is transmitted over a carrier having a different frequency $F_2$ (e.g., near 395 MHz), received by an antenna (RXANT) 13, demodulated by a receiver (RX) 14, and outputted from a speaker (SP) 15.

Figure 4:
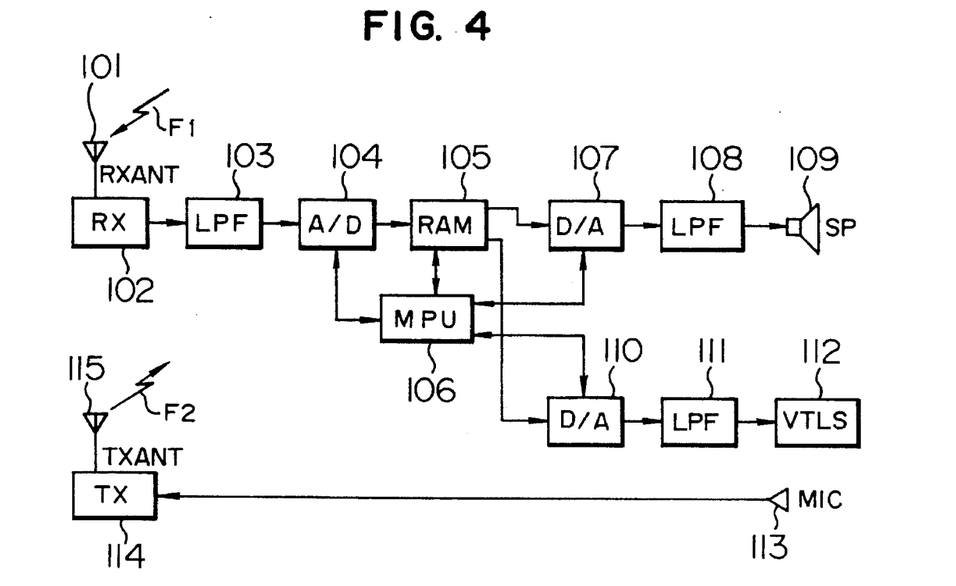
FIG. 4 is a block diagram showing the structure of a base station (multiplex signal receiving side) according to an embodiment of the invention.

FIG. 4 shows the structure of a base station according to an embodiment of the invention. The operation to be performed by the base station will be described. A multiplex signal transmitted from the mobile station over radio waves having the frequency $F_1$ is received by an antenna 101, demodulated by receiver 102, and passed through a low pass filter 103. The demodulated signal from the low pass filter is converted into a digital signal by an A/D converter 104 under the control of an MPU 106 and stored in a RAM 105. This digital signal is subjected to the above-described demodulating process which is controlled by MPU 106 while using RAM 105. The voice signal and vital sign signal are converted into analog signals respectively by D/A converters 107 and 110, and thereafter reproduced. A speech signal inputted to a microphone 113 is supplied to a transmitter 114 and transmitted from an antenna 115 as radio waves having the frequency $F_2$.

The multiplexing and demodulating method described above is readily made applicable to the case where there are a plurality of channels of voice signals and vital sign signals. In the above embodiment, radio communication from a mobile station to a base station via an incoming channel has been described. The invention is also applicable to radio communication from a base station to a mobile station via an outgoing channel, radio communication between mobile stations or between base stations, and wire communication such as telephone lines. A data signal transmitted together with a voice signal is not limited to a vital sign signal, but obviously other signals such as general measurement data and digital data may also be used.

As described so far, a multiplex communication apparatus for voice signals and data signals of this invention achieves very fine multiplex transmission for voice and data signals, even if a data signal to be transmitted, such as an electrocardiogram signal, has important information outside of the pass band of a communication channel. Specifically, on the transmission side, the data signal is compressed through modulation such as delta modulation. The compressed data signal is subjected to a predetermined digital modulation process to transform it into a signal suitable for the characteristics of a communication channel. This signal is then combined with a compressed pressed voice signal to generate a multiplex signal. On the reception side, the multiplex signal is demultiplexed and demodulated by performing the above operations in the reverse order.

In the multiplexing process on the transmission side, both the voice signal and vital sign signal are sampled, and the sample signal is subjected to the time division process, data compression process, digital modulation process, time compression process for the voice signal, and synthesizing process for the voice and vital sign signals. These processes are all performed by using digital signals. The digital signal processing can be realized by using simple means such as a microprocessor and a RAM. These features are also true for the demultiplexing and demodulating process on the reception side. Accordingly, it is possible to realize a multiplex communication apparatus which is very small, light in weight, and cost effective.

A multiplex communication apparatus for voice and data signals can be realized which can set an optimum compression factor from the viewpoint of both the sound quality of a reproduced voice signal and the data transmission speed.

It is also possible to provide a radio communication method for multiplex transmission of voice and data signals, particularly suitable for transmission of data signals such as electrocardiograms, pulse waves, brain waves, and blood pressures, a radio channel.

A radio communication method can also be realized which can reproduce voice and vital sign signals without any interception even if the reception side cannot detect a synchronizing signal used for separating a multiplex signal into voice and vital sign signals.

In a communication system for multiplexing voice and vital sign signals and transmitting a multiplex signal between a base station and a mobile station via a radio channel, a transmitter at the base and mobile stations can be manufactured to be very compact, light in weight, and cost effective.

What is claimed is:

1. An apparatus for multiplex transmission of a voice signal and an analog data signal, comprising:

sampling means for sampling said voice signal and said analog data signal and generating a digital voice signal and a digital data signal, respectively;

time division means for dividing said digital voice signal and said digital data signal on the basis of a predetermined period;

modulation means for modulating said divided digital data signal by a predetermined digital modulation scheme;

means for compressing said divided digital voice signal at a predetermined compression factor to generate a compressed voice signal;

means for combining said divided and compressed voice signal and said divided and digitally modulated digital data signal to generate a multiplex signal in which the divided and digitally modulated digital data signal precedes the divided and compressed voice signal in each of a plurality of the predetermined period;

means for modulating a carrier signal by said multiplex signal; and means for transmitting said modulated carrier signal.

2. An apparatus according to claim 1, further including means for compressing the divided digital data signal to generate a compressed data signal which is supplied to said modulation means, wherein the means for generating the multiplex signal combines said divided and compressed voice signal and said divided, compressed and digitally modulated data signal to generate a multiplex signal.

3. An apparatus according to claim 2, wherein said means for generating said compressed data signal compresses said divided digital data signal by one of a delta modulation scheme and an adaptive delta modulation scheme.

4. An apparatus according to claim 1, wherein at least said voice signal and said data signal are supplied from different channels.

5. An apparatus according to claim 1, further comprising means for adding a synchronizing signal at a predetermined position of said multiplex signal at the predetermined period.

6. An apparatus according to claim 1, wherein said digital modulation scheme is an MSK modulation scheme.

7. An apparatus according to claim 1, wherein said means for generating the compressed voice signal determines the compression factor by the following formula:

$$1-(n \times f/f_2)$$

where n is a positive integer, f is the frequency of said data signal, and $f_2$ is the modulation rate necessary for said digital modulation scheme.

8. An apparatus according to claim 7, wherein the value of n in the formula is given by $n=f/f_1$ and set to be $n \geq 10$ where f1 is the sampling frequency of said voice signal.

9. An apparatus according to claim 1, wherein said means for transmitting said modulated carrier signal includes means for transforming said digital multiplex signal into an analog multiplex signal, whereby said carrier signal is modulated by said analog multiplex signal.

10. An apparatus according to claim 1, wherein said data signal includes vital sign information.

11. A communication apparatus comprising:

a transmitter for transmitting a voice signal and an analog data signal; and a receiver for receiving said voice signal and said analog data signal;

wherein said transmitter includes:

sampling means for sampling said voice signal and said analog data signal to generate a digital voice signal and a digital data signal;

time division means for dividing said digital voice signal and said digital data signal on the basis of a predetermined period;

modulation means for modulating said divided digital data signal by a predetermined digital modulation scheme;

means for compressing said divided digital voice signal at a predetermined compression factor to generate a compressed voice signal;

means for combining said divided and compressed voice signal and said divided and digitally modulated digital data signal to generate a multiplex signal in which the divided and digitally modulated digital data signal precedes the divided and compressed voice signal in each of a plurality of the predetermined period;

means for modulating a carrier signal by said multiplex signal; and means for transmitting said modulated carrier signal as a transmission signal; and wherein said receiver includes:

means for receiving said modulated carrier signal;

means for demodulating said multiplex signal from said received modulated carrier signal;

means for sampling said demodulated multiplex signal and separating said demodulated multiplex signal into said compressed voice signal and said digitally modulated digital data signal;

means for demodulating said separated digital data signal by a predetermined digital demodulation scheme and combining said separated and demodulated digital data signal to reproduce the original data signal; and means for expanding said separated and compressed voice signal at an expansion factor which is an inverse of said compression factor and combining said separated and expanded voice signal to reproduce the original voice signal.

12. A communication apparatus according to claim 11, wherein said transmitter further includes means for compressing said divided digital data signal to generate a compressed data signal which is supplied to said modulation means, said combining means generate said multiple signal is means for combining said divided and compressed voice signal and said divided, digitally modulated, and compressed data signal, and said receiver further includes means for expanding said demodulated and compressed data signal and said means for reproducing said original data signal from said expanded data signal.

13. A communication apparatus according to claim 11, wherein the transmitter further includes means for converting said digital multiplex signal into an analog multiplex signal, and said modulating means is means for modulating said carrier signal by said analog multiplex signal.

14. A communication system comprising:

a base station; and a mobile station connected to said base station through a radio channel;

wherein said mobile station includes:

first means for sampling a plurality of channel signals including a first voice signal and a vital sign signal to generate a digital voice signal and a digital vital sign signal;

second means for dividing said digital voice signal and said digital vital sign signal on the basis of a predetermined period;

third means for modulating said divided digital vital sign signal by one of a delta modulation scheme and an adaptive delta modulation scheme to compress data;

fourth means for modulating said compressed digital vital sign signal by an MSK modulation scheme;

fifth means for compressing said divided digital voice signal at a predetermined compression factor to generate a compressed voice signal;

sixth means for combining said divided and compressed voice signal and said divided and MSK modulated digital vital sign signal to generate a multiplex signal;

seventh means for modulating a carrier signal by said multiplex signal to generate a transmission signal, and transmitting the transmission signal as a first radio wave; and eighth means for receiving a second radio wave transmitted from said base station and for reproducing a second voice signal from said second radio wave; and wherein said base station includes:

ninth means for receiving said first radio wave and demodulating said multiplex signal;

tenth means for sampling said demodulated multiplex signal;

eleventh means for separating said sampled and demodulated multiplex signal into said compressed voice signals and said MSK modulated digital vital sign signals;

twelfth means for demodulating said compressed digital vital sign signals by a predetermined digital demodulation scheme;

thirteenth means for expanding said divided and demodulated digital vital sign signals and for combining said divided vital sign signals to reproduce said original vital sign signal;

fourteenth means for expanding said divided and compressed voice signals at an expansion factor which is an inverse of said compression factor and for combining said separated and expanded voice signal to reproduce said original first voice signal;

fifteenth means for modulating a carrier signal by said second voice signal and for generating said second radio wave; and sixteenth means for transmitting said second radio wave to said mobile station.

15. A communication system according to claim 14, wherein said seventh means of said mobile station further includes means for converting said digital multiplex signal into an analog multiplex signal so that the carrier signal is modulated by the analog multiplex signal.

16. A communication system according to claim 15, wherein said second, third, fourth, fifth, and sixth means include a microprocessor and a RAM, said micro-processor controlling read/write of said digital voice signal and said digital vital sign signal from/to said RAM in accordance with a predetermined control program.

17. A communication system according to claim 15, wherein said mobile station further includes means for adding a synchronizing signal to a predetermined position of said multiplex signal at a predetermined period, and said base station further includes means for detecting the synchronizing signal from said received first radio wave, whereby said compressed voice signal and said MSK modulated vital sign signal are separated from said multiplex signal on the basis of said synchronizing signal.

18. A communication system according to claim 17, wherein said eleventh means includes timer means for generating a reference signal in synchronization with the period of said synchronizing signal, and when the base station cannot detect said synchronizing signal, said compressed voice signal and said MSK modulated vital sign signal are separated from said multiplex signal on the basis of said reference signal.

19. A communication method for a radio communication system having a base station and a mobile station connected to said base station through a radio channel, wherein said communication method for said mobile station comprises the steps of:

sampling a plurality of channel signals including a voice signal and a vital sign signal to generate a digital voice signal and a digital vital sign signal;

dividing said digital voice signal and said digital vital sign signal on the basis of a predetermined period;

modulating said divided digital vital sign signal by one of a delta modulation scheme and an adaptive delta modulation scheme to compress data;

modulating said divided digital voice signal by an MSK modulation scheme;

compressing said divided digital voice signal at a predetermined compression factor to generate a compressed voice signal;

combining said divided and compressed voice signal and said divided and MSK modulated digital vital sign signal to generate a multiplex signal;

modulating a carrier signal by said multiplex signal to generate a transmission signal;

transmitting the transmission signal as a first radio wave; and receiving a second radio wave transmitted from said base station and reproducing a voice signal from said second radio wave, and the communication method for said base station comprises the steps of:

receiving said first radio wave and demodulating the multiplex signal;

sampling said demodulated multiplex signal;

separating said sampled and demodulated multiplex signal into said compressed voice signal and the MSK modulated digital vital sign signal;

demodulating said separated digital vital sign signal by a predetermined digital demodulation scheme;

expanding said separated and demodulated digital vital sign signal and combining the divided vital sign signal to reproduce said original vital sign signal;

expanding said separated and compressed voice signal at an expansion factor which is an inverse of said compression factor and combining the separated and expanded voice signals to reproduce the original voice signal;

modulating a carrier signal by said voice signal to generate said second radio wave; and transmitting said second radio wave to said mobile station.

20. A communication method according to claim 19, wherein said communication method for said mobile station further includes the step of converting the digital multiplex signal into an analog multiplex signal, whereby said carrier signal is modulated by the analog multiplex signal.

21. A communication method according to claim 20, wherein said communication method for said mobile station further includes the step of adding a synchronizing signal to a predetermined position of said multiplex signal at the predetermined period, and said communication method for said base station further includes the step of detecting said synchronizing signal from said received first radio wave, so that said compressed voice signal and said MSK modulated vital sign signal are separated from said multiplex signal on the basis of said synchronizing signal.

22. A communication method according to claim 21, wherein when said base station cannot detect said synchronizing signal, said compressed voice signal and said MSK modulated vital sign signal are separated from said multiplex signal on the basis of a signal synchronized with the period of said synchronizing signal.

* * * * *